(12) United States Patent
Studer et al.

(10) Patent No.: US 10,181,007 B2
(45) Date of Patent: Jan. 15, 2019

(54) DEVICE AND METHOD FOR MODELLING A CORNEA

(71) Applicant: Optimo Medical AG, Biel (CH)

(72) Inventors: Harald P. Studer, Liebefeld (CH); Hansjörg Riedwyl, Biel (CH); Philippe Büchler, Gossens (CH); Cynthia J. Roberts, Columbus, OH (US)

(73) Assignee: Optimo Medical AG, Biel (CH)

( * ) Notice: Subject to any disclaimer, the term of this patent is extended or adjusted under 35 U.S.C. 154(b) by 424 days.

(21) Appl. No.: 14/903,674

(22) PCT Filed: Jun. 30, 2014

(86) PCT No.: PCT/EP2014/001791
§ 371 (c)(1),
(2) Date: Jan. 8, 2016

(87) PCT Pub. No.: WO2015/003779
PCT Pub. Date: Jan. 15, 2015

(65) Prior Publication Data
US 2016/0162630 A1 Jun. 9, 2016

(30) Foreign Application Priority Data
Jul. 10, 2013 (EP) .................................... 13003481

(51) Int. Cl.
*G06F 17/50* (2006.01)
*G06F 19/12* (2011.01)
(Continued)

(52) U.S. Cl.
CPC .............. *G06F 19/12* (2013.01); *A61B 34/10* (2016.02); *A61F 9/00825* (2013.01);
(Continued)

(58) Field of Classification Search
USPC ........................................ 703/2, 5, 7; 378/65
See application file for complete search history.

(56) References Cited

U.S. PATENT DOCUMENTS

| | | | |
|---|---|---|---|
| 8,457,277 B2 * | 6/2013 | Gertner | A61N 5/10 378/65 |
| 2008/0187101 A1 * | 8/2008 | Gertner | A61N 5/1017 378/65 |

(Continued)

FOREIGN PATENT DOCUMENTS

| | | |
|---|---|---|
| WO | WO 94/18636 A2 | 8/1994 |
| WO | WO 02/07660 A2 | 1/2002 |

OTHER PUBLICATIONS

International Search Report dated Jan. 13, 2015.
(Continued)

*Primary Examiner* — Thai Q Phan
(74) *Attorney, Agent, or Firm* — Walter | Haverfield LLP; D. Peter Hochberg; Sean F. Mellino (57) ABSTRACT

A patient-specific finite element model of the cornea is generated for the purposes of modeling a cornea for simulating tissue cuts in the cornea. A first group of tissue fibers, with main fibers that extend parallel to the surface of the cornea, is distributed in the finite element model in accordance with a first distribution function. Moreover, a second group of tissue fibers, with inclined cross-linked fibers that do not extend parallel to the surface of the cornea, is distributed in the finite element model in accordance with a second distribution function. Here, the second distribution function distributes the cross-linked fibers with a non-uniform weighting function over the depth of the cornea, from the outer surface of the cornea to the inner surface of the cornea.

14 Claims, 4 Drawing Sheets

(51) Int. Cl.
  A61F 9/008 (2006.01)
  A61B 34/10 (2016.01)
  G16H 50/50 (2018.01)
  G06F 19/00 (2018.01)
  A61F 9/013 (2006.01)
(52) U.S. Cl.
  CPC .......... *G06F 17/5009* (2013.01); *G06F 19/00* (2013.01); *G16H 50/50* (2018.01); *A61B 2034/105* (2016.02); *A61F 9/013* (2013.01); *A61F 2009/00853* (2013.01); *A61F 2009/00897* (2013.01)

(56) References Cited

U.S. PATENT DOCUMENTS

| 2009/0003525 | A1* | 1/2009 | Gertner | A61N 5/10 378/65 |
| 2009/0187386 | A1* | 7/2009 | Bille | G16H 50/50 703/2 |
| 2009/0318907 | A1 | 12/2009 | Bille et al. | |
| 2010/0166148 | A1* | 7/2010 | Gertner | A61N 5/10 378/65 |
| 2010/0254513 | A1* | 10/2010 | Gertner | A61N 5/1017 378/65 |
| 2011/0170664 | A1* | 7/2011 | Gertner | A61N 5/10 378/65 |
| 2011/0228908 | A1* | 9/2011 | Gertner | A61N 5/10 378/65 |
| 2011/0268250 | A1* | 11/2011 | Gertner | A61N 5/10 378/65 |
| 2012/0076272 | A1* | 3/2012 | Gertner | A61N 5/1017 378/65 |

OTHER PUBLICATIONS

Written Opinion of the International Searching Authority dated Jan. 13, 2015.
International Preliminary Report on Patentability dated Jan. 12, 2016.
Harald P. Studer et al., Patient-specific finite-element simulation of the human cornea: A clinical validation study on cataract surgery, Journal of Biomechanics, Feb. 1, 2013, p. 751-758, vol. 46, No. 4.
H. Studer et al., Biomechanical model of human cornea based on stromal microstructure, Journal of Biomechanics, Mar. 22, 2010, p. 836-842, vol. 43, No. 5, Pergemon Press, NY,NY,USA.
Abahussin et al, 3D Collagen Orientation Study of Human Cornea Using X-ray Diffraction and Femtosecond Laser Technology, Invest Ophthalmol Vis Sci., Jun. 10, 2009, p. 5159-5164, vol. 50, No. 10.
Andrew J. Quantock et al., Small-angle fibre diffraction studies of corneal matrix structure: a depth-profiled investigation of the human eye-bank cornea, Journal of Applied Crystallography, 2007, p. 335-340, vol. 40.
B.P. Palma et al., Reduced Collagen Interfibrillar Spacing in Macular Corneal Dystrophy Occurs Predominantly in Deep Stromal Layers, Investigative Ophthalmology & Visual Science, May 2008, p. 3926, vol. 49.
CS Kamma-Lorger et al., Depth profile study of molecular collagen structure in normal human cornea, Acta Ophthalmologica, 2008, p. 243, vol. 86.
Keith M. Meek et al., The use of Xray scattering techniques to quantify the orientation and distribution of collagen in the corneal stroma, Progress in Retinal and Eyre Research, 2009, p. 369-392, vol. 28.
Christina S. Kamma-Lorger et al., Collagen and mature elastic fibre organisation as a function of depth in the human cornea and limbus. Journal of Structural Biology, 2010, p. 424-430, vol. 169.
Steven J. Petsche et al., Depth-Dependent Transverse Shear Properties of the Human Corneal Stroma, Investigative Ophthalmology & Visual Science, Feb. 2012, p. 873-880, vol. 53, No. 2.
Michael. R. Bryant et al., Constitutive Laws for Biomechanical Modeling of Refractive Surgery, Journal of Biomechanical Engineering, Nov. 1996, p. 473-481, vol. 118.
Peter M. Pinsky et al., Computational modeling of mechanical anisotropy in the cornea and sclera, Journal of Cataract and Refractive Surgery, 2005, p. 136-145, vol. 31.
V. Alastrue et al., Biomechanical Modeling of Refractive Corneal Surgery, Journal of Biomechanical Engineering, Feb. 2006, p. 150-160, vol. 128.
Elena Lanchares et al, Finite element simulation of arcuates for astigmatism correction, Journal of Biomechanics, 2008, p. 797-805, vol. 41.
A. Pandolfi et al., A model for the human cornea: constitutive formulation and numerical analysis, Biomechanios and Modeling in Mechanobiology, 2006, p. 237-246, vol. 5.
Anna Pandolfi et al., Three-dimensional Modeling and Computational Analysis of the Human Cornea Considering Distributed Collagen Fibril Orientations, Journal of Biomechanical Engineering, Dec. 2008, p. 061006-1-061006-12, vol. 130.
Anna Pandolfi et al., Finite element simulations of laser refractive corneal surgery, Engineering with Computers, 2009, p. 15-24, vol. 25.
Steven J. Petsche et al., The role of 3-D collagen organization in stromal elasticity: a model based on X-ray diffraction data and second harmonic-generated images, Biomechanics and Modeling in Mechanobiology, 2013.

* cited by examiner

DEVICE AND METHOD FOR MODELLING A CORNEA

CROSS REFERENCE TO RELATED APPLICATIONS

This application is a 371 National State application of International Application No. PCT/EP2014/001791 filed on Jun. 30, 2014, which claims priority of European Serial Number 13003481.2 filed on Jul. 10, 2013, both of which are incorporated herein by reference in their entireties.

BACKGROUND OF THE INVENTION

1. Field of the Invention

The present invention relates to a device and a method for modeling a cornea. In particular, the present invention relates to a computerized device and a computer-implemented method for modeling a cornea for simulating tissue cuts in the cornea, wherein the computerized device comprises a processor programmed to generate a patient-specific finite element model of the cornea.

2. Description of the Prior Art

A plurality of refractive errors such as myopia (short-sightedness), hyperopia (farsightedness) or astigmatism are corrected these days by means of surgical interventions on the eye. Here, the refractive correction of the eye is predominantly brought about by means of ophthalmological laser systems, which cut and/or ablate the eye tissue, in particular the cornea, in order to approximate the optical refractive power of the eye as closely as possible to a desired value. Although tissue cuts can be carried out very precisely by means of laser pulses—much more accurately compared to e.g. manually using a scalpel—the change in the tissue form emerging in the case of tissue cuts as a result of the intraocular pressure makes the planning of cuts and the prediction of cut results nevertheless very difficult.

In order to improve the ophthalmic refractive correction, WO 02/07660, WO 94/18636, US 2009/318907 and US 2009/187386 describe the modeling of the eye using finite element analysis. Here, the finite element model of the eye can be used for simulating tissue cuts. WO 02/07660 describes the introduction of a layer model of the cornea with a plurality of layers with different strengths. US 2009/318907 and US 2009/187386 describe a general axis-symmetrical model based on a nonlinear elastic, slightly compressible and transversely isotropic formulation. US 2009/187386 moreover describes a connection of the cornea to the sclera with pre-programming of peripheral elements for imaging a secure connection of the cornea to the sclera (limbus), which may not be sufficient in the case of cuts which extend beyond the cornea into the adjacent sclera. Moreover, the known solutions provide no indications as to how the stromal swelling pressure is included in the modeling.

In recent years, the inhomogeneity of the cornea over the depth thereof was examined in great detail, particularly in:

Quantock A J, Boote C, Yount R D, Hayes S, Tanioka H, Kawasaki S, Ohta N, Iida T, Yagi N, Kinoshita S, Meek K M, (2007); "Small-angle fibre diffraction studies of corneal matrix structure: a depth-profiled investigation of the human eye-bank cornea"; Journal of Applied Crystallography, 40: 335-340;

Palka B P, Tanioka H, Sotozono C, Yagi N, Boote C, Young R D, Meek K M, Quantock A J, (2008); "Reduced collagen interfibrillar spacing in macular corneal dystrophy occurs predominantly in deep stromal layers"; Investigative Ophthalmology & Visual Science, 49: E-Abstract 3926;

Kamma-Lorger C S, Boote C, Young R D, Hayes S, Quantock A J, Meek K M, (2008); "Depth profile study of molecular collagen structure in normal human cornea; Acta Ophthalmologica", 86: 243;

Meek K M, Boote C, (2009); "The use of X-ray scattering techniques to quantify the orientation and distribution of collagen in the corneal stroma"; Progress in Retinal and Eye Research, 28: 369-392;

Kamma-Lorger C S, Boote C, Hayes S, Moger J, Burghammer M, Knupp C, Quantock A J, Sorensen T, Di Cola E, White N, Young R D, Meek K M, (2010); "Collagen and mature elastic fibre organization as a function of depth in the human cornea and limbus"; Journal of Structural Biology, 169: 424-430; and Petsche S J, Chernayak D, Martiz J, Levenston M E, Pinsky P M, (2012); "Depth-Dependent Transverse Shear Properties of the Human Corneal Stroma"; Investigative Ophthalmology & Visual Science, 53(2): 873-80.

What was identified here is that the tissue becomes ever weaker over the depth thereof, i.e. from the front/outside (anterior) to the back/inside (posterior), and, in particular, that there is a significant reduction in the shearing stiffness. The cause of this was found to lie in the fact that there are many inclined collagen fibers, i.e. collagen fibers that do not extend parallel to the corneal surface, in the front/outer layers. Inclined fibers, or so-called cross-linked fibers, provide the tissue with shearing stiffness. By contrast, the fibers lying properly on one another in layers, extending parallel to the surface, are found in the deep (back/inside) layers.

In the last decade, various mathematical material definitions were established and published for simulating the biomechanical properties of the corneal tissue, particularly in:

Bryant M, McDonnell P, (1996); "Constitutive laws for biomechanical modelling of refractive surgery", Journal of Biomechanical Engineering, 118(4): 473-481;

Pinsky P M, Van der Heide D, Chernyak D, (2005); "Computational modelling of mechanical anisotropy in the cornea and sclera"; Journal of Cataract and Refractive Surgery, 31(1): 136-145;

Alastrue V, Calvo B, Pena E, Doblare M, (2006); "Biomechanical Modelling of Refractive Surgery; Journal of Biomechanical Engineering", 128: 150;

Lanchares E, Calvo B, Cristobal J, Doblare M, (2008); "Finite element simulation of arcuates for astigmatism correction"; Journal of Biomechanics, 41: 797-805;

Pandolfi A, Manganiello F, (2006); "A model for the human cornea: constitutive formulation and numerical analysis"; Biomechanics and Modelling in Mechanobiology, 5(4): 237-246;

Pandolfi A, Holzapfel G, (2008); "Three-dimensional modelling and computational analysis of the human cornea considering distributed collagen fibril orientations"; Journal of Biomechanical Engineering, 130(6); and Pandolfi A, Fotia G, Manganiello F, (2009); "Finite element simulation of laser refractive corneal surgery"; Engineering with Computers, 25: 15-24.

Generating a patient-specific finite element model of the cornea was described in the document Studer H P, Riedwyl H, Amstutz C A, Hanson V M, Büchler P, (2013) "Patient-specific finite-element simulation of the human cornea: A clinical validation study on cataract surgery"; Journal of Biomechanics, 46(4): 751-758. Here, the effect of cataract incisions on patients was simulated numerically. However, Studer et al. specifically state in this document that neither the material parameters nor the distribution of collagen fibers was patient-specific and that the depth-dependence of mechanical properties within the corneal thickness was also ignored. Moreover, as a conclusion, they noted that taking into account the individual corneal topography of the patient is more relevant to a precise prediction of the post-operative corneal form than a precise determination of patient-specific material properties.

Mathematical material definitions for simulating the biomechanical properties of the corneal tissue, in which the inclined fibers are also taken into account, are only found in the following documents:

Studer H P, Larrea X, Riedwyl H, Büchler P, (2010); "Biomechanical model of human cornea based on stromal microstructure"; Journal of Biomechanics, 43: 836-842; and Petsche S J, Pinsky P M, (2013); "The role of 3-D collagen organization in stromal elasticity: a model based on X-ray diffraction data and second harmonic-generated images"; Biomechanics and Modelling in Mechanobiology.

Here, in the latter document, Petsche S J and Pinsky P M define a three-dimensional distribution function (all directions are in a spherical coordinate system), which simultaneously models the weighting of the main fibers and inclined fibers. By means of this weighting, the authors describe the amount of collagen fibers that extend in a specific direction. The fibers themselves are described as a material anisotropy in the continuum.

BRIEF SUMMARY OF THE INVENTION

It is an object of the present invention to propose a device and a method for modeling a cornea, which enable the simulation of tissue cuts in the cornea. In particular, it is an object of the present invention to propose a device and a method for modeling a cornea which do not have at least some of the disadvantages of the known systems.

In accordance with the present invention, these objects are achieved by the features of the independent claims. Moreover, further advantageous embodiments emerge from the dependent claims and the description.

A computerized device for modeling a cornea for simulating tissue cuts in the cornea comprises a processor programmed to load patient-specific corneal data, generate a patient-specific finite element model of the cornea and determine elements in the finite element model which are separated from one another by the tissue cuts on the basis of cut data defining the tissue cuts.

The present invention achieves the aforementioned objects by virtue of in particular, the processor of the computerized device moreover being programmed to distribute a first group of tissue fibers, with main fibers that extend parallel to the outer surface of the cornea, in the finite element model in accordance with a first distribution function and to distribute a second group of tissue fibers, with inclined cross-linked fibers that do not extend parallel to the outer surface of the cornea, in the finite element model in accordance with a second distribution function, wherein the second distribution function distributes the cross-linked fibers with a non-uniform, decreasing depth distribution function over the depth of the cornea, from the outer surface of the cornea to the inner surface of the cornea.

In an embodiment variant, the processor is programmed to distribute the cross-linked fibers over the depth of the cornea with a depth distribution function having a sinusoidal profile. The depth distribution function has a sinusoidal profile in at least one defined portion (e.g. in a third) of the thickness or depth of the cornea, wherein said sinusoidal profile is restricted to a portion of the sinusoidal curve which defines a decreasing depth distribution of the cross-linked fibers from the outer surface of the cornea to the inner surface of the cornea.

In an embodiment variant, the processor is programmed to introduce permeability values for liquid exchange in the corneal tissue into the finite element model, which permeability values are dependent on the depth of the cornea.

In an embodiment variant, the processor is programmed to introduce permeability values for liquid exchange in the corneal tissue into the finite element model, which permeability values are dependent on the depth distribution function, by means of which the cross-linked fibers are distributed over the depth of the cornea.

In an embodiment variant, the processor is programmed to generate a transition from the patient-specific finite element model of the cornea to a population-based sclera model and to distribute the cross-linked fibers in the transition with a decreasing depth distribution function over the depth of the transition, from an outer transition surface, which extends from the outer surface of the cornea to the outer surface of the sclera, to an inner transition surface, which extends from the inner surface of the cornea to the inner surface of the sclera.

In an embodiment variant, the processor is programmed to distribute the cross-linked fibers on a number of layers that extend parallel to the outer surface of the cornea in the finite element model and to distribute the cross-linked fibers in the layers, respectively with a two-dimensional distribution function.

In an embodiment variant, the processor is programmed to store different material properties for the first group of tissue fibers and the second group of tissue fibers in the finite element model.

In an embodiment variant, the processor is programmed, in the finite element model, to distribute the main fibers uniformly on a plurality of areas, or layers, that extend parallel to the outer surface of the cornea and to distribute said main fibers on the areas, or in the layers, with in each case a two-dimensional distribution function.

In addition to the computerized device for modeling a cornea, the present invention moreover relates to a computer-implemented method for modeling a cornea for simulating tissue cuts in the cornea and to a computer program product comprising a non-transient computer-readable medium with computer program code stored thereon, which computer program code is configured to control a processor in such a way that the processor executes the method for modeling the cornea. The computer-implemented method comprises the execution of the following steps by the processor: loading patient-specific corneal data, generating a patient-specific finite element model of the cornea; distributing a first group of tissue fibers, with main fibers that extend parallel to the outer surface of the cornea, in the finite element model in accordance with a first distribution function; and distributing a second group of tissue fibers, with inclined cross-linked fibers that do not extend parallel to the outer surface of the cornea, in the finite element model in accordance with a second distribution function, wherein the second distribution function distributes the cross-linked fibers with a non-uniform depth distribution function over the depth of the cornea, from the outer surface of the cornea to the inner surface of the cornea, and determining elements in the finite element model which are separated from one another by the tissue cuts on the basis of cut data defining the tissue cuts.

BRIEF DESCRIPTION OF THE DRAWINGS

Below, an embodiment of the present invention is described on the basis of an example. The exemplary embodiment is illustrated by way of the following attached figures.

DETAILED DESCRIPTION OF THE PREFERRED EMBODIMENTS

Figure 1:
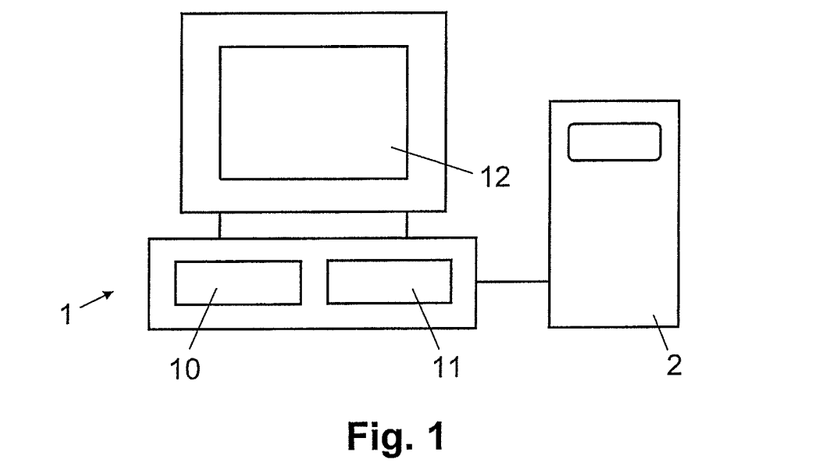
FIG. 1 shows a block diagram of a computerized device for modeling a cornea for simulating tissue cuts in the cornea.

In FIG. 1, reference sign 1 relates to a computerized device for modeling a cornea for simulating tissue cuts in the cornea. The device 1 comprises an operational computer with at least one processor 10 and storage 11, connected to the processor 10, for storing data (data storage) and computer program code (program storage). In the embodiment in accordance with FIG. 1, the device 1 moreover comprises a display 12, e.g. an LED or LCD monitor. As depicted schematically in FIG. 1, the device 1 is connected in a variant to a computerized data source 2 external to the device 1, for example by way of a wired or wireless communication interface. The data source 2 comprises one or more processors and it is configured to transmit eye data, including patient-specific corneal data and/or population-based sclera data, to the device 1, as will be described in more detail below. Depending on the embodiment variant, the data source 2 comprises an ophthalmological measuring device for acquiring the patient-specific corneal data from a patient and/or an ophthalmological database with population-based sclera data.

The processor 10 is configured or programmed to execute a method for modeling a cornea for simulating tissue cuts in the cornea. To this end, the device 1 comprises a computer program product with a computer-readable medium, which is permanently or removably connected to the processor 10 and which comprises computer program code stored thereon, said computer program code being configured to control the processor 10 in such a way that the latter executes the method. In the following paragraphs, possible sequences of steps for executing the method are described with reference to FIGS. 2, 3 and 4.

Figure 2:
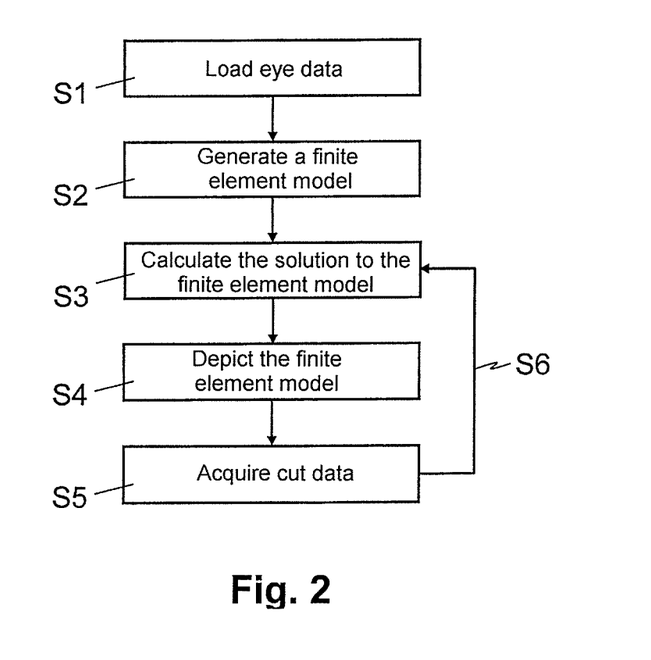
FIG. 2 shows a flowchart with an exemplary sequence of steps of a method for modeling a cornea for simulating tissue cuts in the cornea.

As depicted in FIG. 2, eye data are loaded into the storage 11 in step S1.

Figure 3:
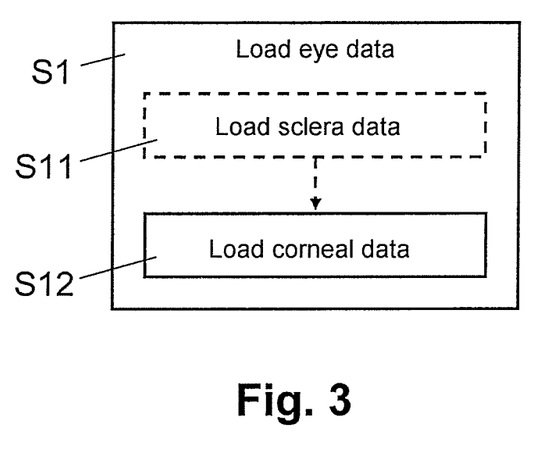
FIG. 3 shows a flowchart with an exemplary sequence of steps for loading eye data.

As can be seen in FIG. 3, population-based sclera data are loaded into the storage 11 in the optional step S11 in this case. The population-based sclera data define a geometric average model of the sclera, including three-dimensional geometry and dimensions of an average sclera on a statistical data basis. In one embodiment variant, the sclera data define at least the geometry and the dimensions of a boundary region of the sclera, which adjoins the transition to the cornea. By way of example, the sclera data are acquired from an Internet-based data source or are permanently stored in the data storage 11.

In step S12, patient-specific corneal data are loaded into the storage 11. The patient-specific corneal data define a patient-specific geometric model of the cornea, including three-dimensional geometry and dimensions of the cornea of a patient on a data basis acquired by measurement. The patient-specific corneal data are preferably acquired by means of an ophthalmological measuring device and stored in the data storage 11 in a manner assigned to the relevant patient.

As depicted schematically in FIG. 2, the processor 10 generates an initial finite element model in step S2 on the basis of the loaded eye data, in particular a patient-specific finite element model of the cornea on the basis of the patient-specific corneal data.

In an embodiment variant, a spherical finite element grid is initially produced, which is transformed by means of a transformation method (warping method) into the patient specific geometry of the cornea 34 (which is defined by the patient-specific corneal data), for example by means of a transformation method as described in Studer H P, Riedwyl H, Amstutz C A, Hanson V M, Büchler P, (2013) "Patient-specific finite-element simulation of the human cornea: A clinical validation study on cataract surgery"; Journal of Biomechanics, 46(4): 751-758.

Figure 4:
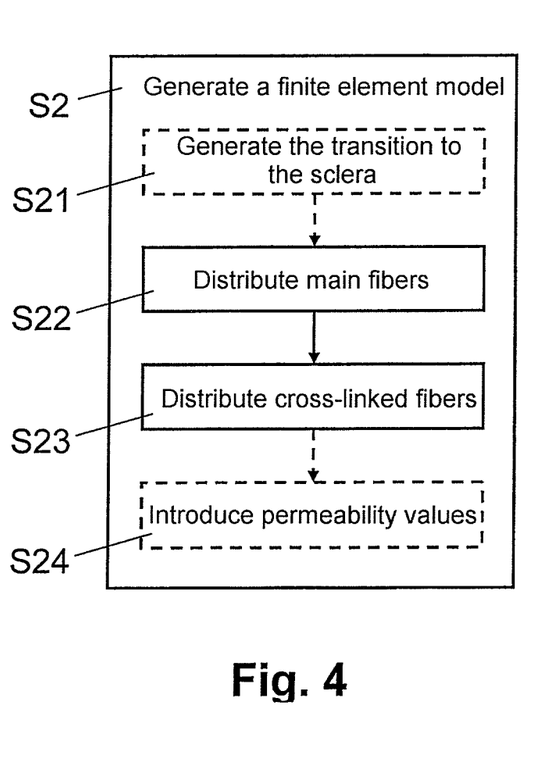
FIG. 4 shows a flowchart of an exemplary sequence of steps for generating a finite element model of a cornea for simulating tissue cuts in the cornea.
Figure 7:
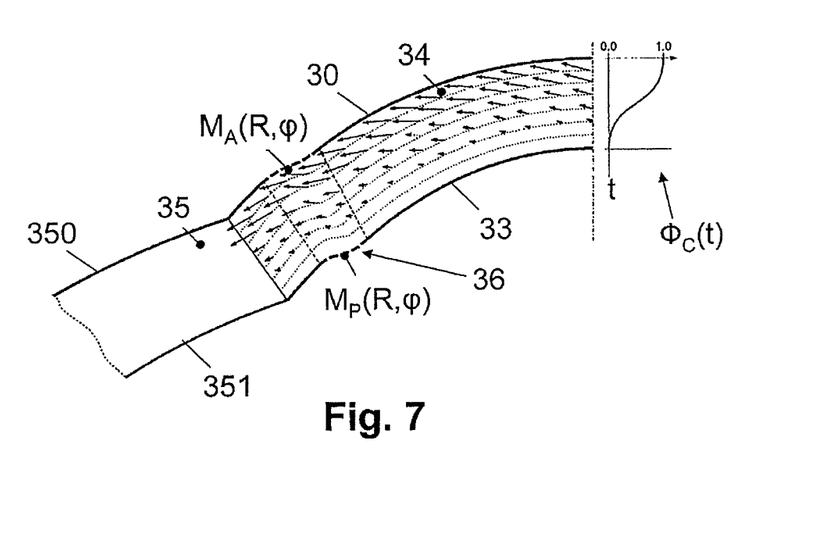
FIG. 7 schematically shows, in a cross section, a transition from a corneal segment to an adjoining sclera segment and the distribution of inclined cross-linked fibers that do not extend parallel to the surface of the cornea over the depth of the cornea and the depth of the transition.

As can be seen in FIG. 4, a transition from the patient-specific cornea to the population-based sclera is generated by the processor 10 in the optional step S21. This is advantageous because part of the sclera is also simulated for a precise simulation of surgical interventions. As illustrated in FIG. 7, a smooth geometric transition 36 is generated from the patient-specific cornea 34 to the population-based sclera 35. In particular, mathematical functions for geometric surfaces are defined for the transition 36 from the patient-specific cornea 34 to the population-based sclera 35, namely a function $M_A(R,\varphi)$ for the front/outer transition surface (anterior) and a function $M_P(R,\varphi)$ for the back/inner transition surface (posterior). The front/outer transition surface $M_A(R,\varphi)$ is realized as a smooth surface and it extends continuously from the front/outer surface 30 of the cornea 34 to the front/outer surface 350 of the sclera 35. The back/inner transition surface $M_P(R,\varphi)$ is realized as a smooth surface and it extends continuously from the back/inner surface 33 of the cornea 34 to the back/inner surface 351 of the sclera 35. Depending on the embodiment variant, the transition 36 is generated on the basis of the patient-specific geometry model of the cornea 34, loaded in step S1, or on the basis of the corresponding finite element model of the cornea 34.

Figure 5:
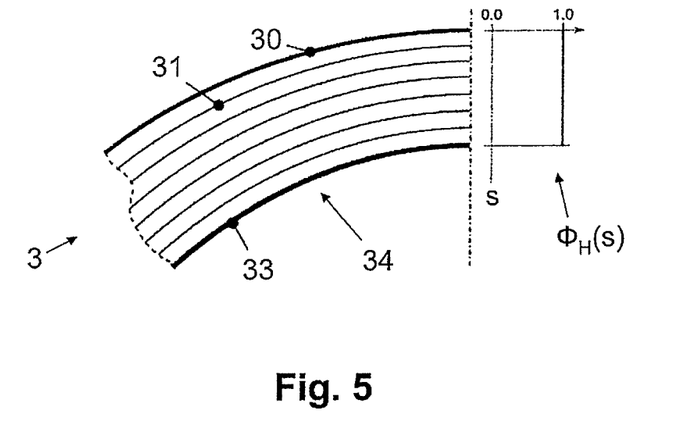
FIG. 5 schematically shows, in a cross section of a corneal segment, the distribution of main fibers that extend parallel to the surface of the cornea over the depth of the cornea (depth distribution) and a corresponding distribution function or depth distribution function or weighting function.

In step S22, the processor 10 distributes the main fibers 31 that extend parallel to the surface 30 of the cornea, as depicted in FIG. 5, in the patient-specific finite element model of the cornea 34. Optionally, the main fibers 31 are accordingly also distributed in the transition 36 from the patient-specific cornea 34 to the population-based sclera 35.

The main fibers 31 are distributed on layers or areas of the cornea 34, which respectively extend at different depths, parallel to the corneal surface 30. Here, use is made of a two-dimensional distribution function $\Phi_{2D}$ (see the example in FIG. 8) to distribute the main fibers 31 within respectively one of these corneal layers (in plane). Here, this two-dimensional distribution function $\Phi_{2D}$ consists of two parts:

$$\Phi_a(R,\varphi;\theta) = \cos^{2n}\theta + \sin + c_1,$$

$$\Phi_b(R,\varphi;\theta) = \sin^{2n}(\theta-\varphi) + c_2 \quad (1)$$

which are combined as follows:

$$\Phi_{2D}(R,\varphi;\theta) = w \cdot \Phi_a(R,\varphi;\theta) + (1-w) \cdot \Phi_b(R,\varphi;\theta). \quad (2)$$

The weighting w between the two parts depends on the location of a material point $P_{R\varphi}$ on the corneal layer and it is given by:

$$w = \begin{cases} 1.0 & \text{if } 0 < R < 4.0 \\ \frac{1}{2}\cos\left[\frac{\pi}{1.5}(R-4.0)\right] + \frac{1}{2} & \text{if } 4.0 < R < 5.5, \\ 0.0 & \text{otherwise} \end{cases} \quad (3)$$

where R is the distance of the material point $P_{R\varphi}$ from the corneal center (0, 0), $\varphi$ is the angle between the positive x-axis in the model and the link between the material point $P_{R\varphi}$ and the corneal center, and $\theta$ defines the fiber direction in the local coordinate system of the material point $P_{R\varphi}$.

A first depth distribution function $\Phi_H(s)$ is used for the distribution (weighting) of the main fibers 31 on the individual corneal layers. In the example of FIG. 5, the first depth distribution function $\Phi_H(s)$ is uniform (constant), i.e. the main fibers 31 are distributed uniformly over the depth s, from the front corneal surface 30 to the back corneal surface 33, and there are the same number of main fibers 31 at each corneal depth (in each corneal layer):

$$\Phi_H(s) = 1. \quad (4)$$

Figure 8:
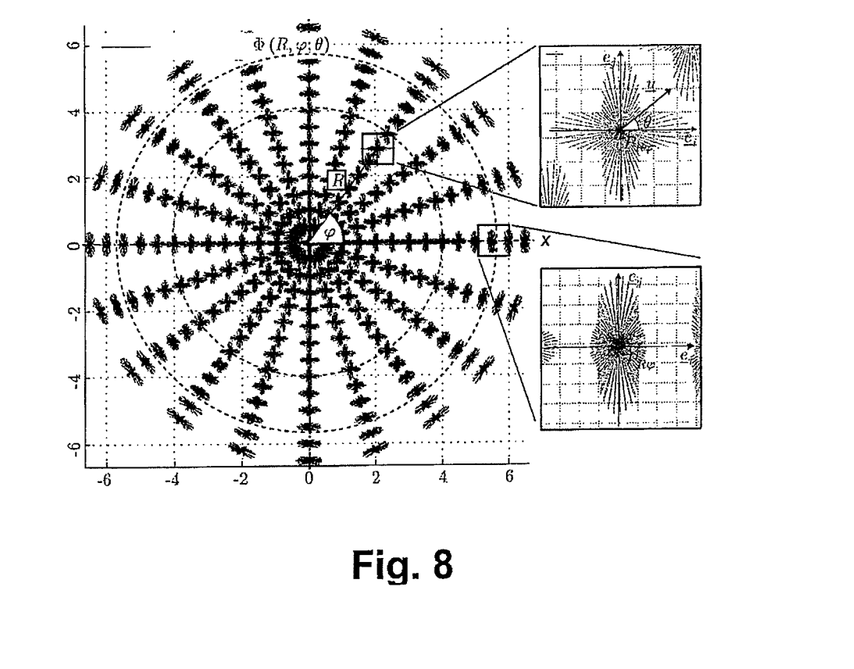
FIG. 8 shows a two-dimensional distribution function for main fibers that extend parallel to the surface of the cornea and inclined cross-linked fibers that do not extend parallel to the surface of the cornea.

Accordingly, the main fibers 31 are distributed independently of the depth and parallel to the surface 30 in accordance with equations (1) to (3), as illustrated in FIG. 8. A person skilled in the art will understand that a different depth distribution function $\Phi_H(s)$ can also be used for the main fibers 31 on account of different anatomical circumstances.

Since parts of the transition 36 from the cornea to the sclera 35 are corneal tissue, the fiber distribution is also applied in the transition 36. In the transition 36 from the patient-specific cornea 34 to the population-based sclera 35, the main fibers 31 are also distributed in the same manner as in the cornea 34, within the parallel layers (areas) by means of the two-dimensional distribution function $\Phi_{2D}$ and over the depth s in accordance with the uniform first depth distribution function (weighting function) $\Phi_H(s)$. The homogeneous depth distribution of the main fibers 31 is depicted schematically in FIGS. 5 and 7 in such a way that the main fibers 31 are depicted as layers or areas extending parallel to the corneal surface 30.

Figure 6:
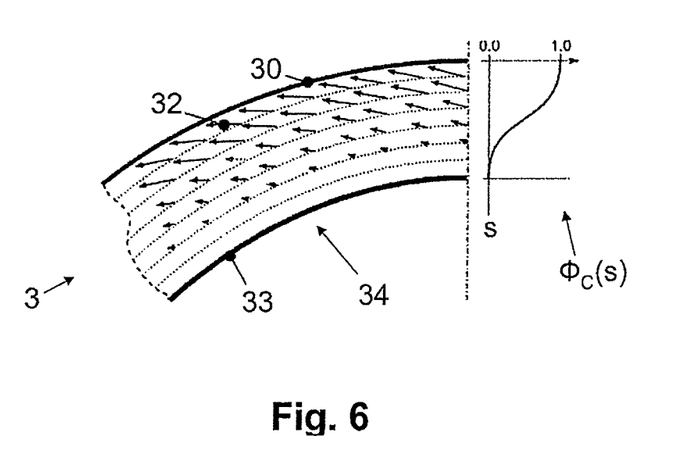
FIG. 6 schematically shows, in a cross section of a corneal segment, the distribution of inclined cross-linked fibers that do not extend parallel to the surface of the cornea over the depth of the cornea (depth distribution) and a corresponding distribution function or depth distribution function or weighting function.

In step S23, the processor 10 distributes the inclined cross-linked fibers 32 that do not extend parallel to the surface 30 of the cornea, as depicted in FIG. 6, in the patient-specific finite element model of the cornea 34. Optionally, the cross-linked fibers 32 are accordingly also distributed in the transition 36 from the patient-specific cornea 34 to the population-based sclera 35.

Hence, the cross-linked fibers 32 are a fiber family differing from the main fibers 31, which cross-linked fibers are inclined by approximately 15° (wherein the inclination should be understood to mean a deviation from the direction of the main fibers), alternately "toward the inside", i.e. inclining toward the surface 33, and "toward the outside", i.e. inclining toward the surface 30. In a variant, different material properties are assigned to the main fibers 31 and the cross-linked fibers 32.

Like the main fibers 31, the cross-linked fibers 32 are distributed within the corneal layers or areas extending parallel to the corneal surface 30 (in plane) by means of the two-dimensional distribution function $\Phi_{2D}$ in accordance with equations (1) to (3) described above.

A second depth distribution function $\Phi_C(s)$ is used for the distribution (weighting) of the cross-linked fibers 32 on the individual corneal layers. In the example of FIG. 6, the second depth distribution function (weighting function) $\Phi_C(s)$ has a profile decreasing with depth s. That is to say, the cross-linked fibers 32 are distributed with a decreasing number over the depth s from the front corneal surface 30 to the back corneal surface 33. In contrast to the depth distribution of the main fibers 31, the cross-linked fibers 32 are therefore not distributed uniformly (i.e. not in a constant manner) but with a specific depth distribution function or weighting function over the depth s. In the example of FIG. 6, the second depth distribution function $\Phi_C(s)$ has a sinusoidal profile (at least in a defined portion of the thickness or depth s of the cornea 34) and it is defined as follows:

$$\Phi_C(s) = \begin{cases} 1.0 & \text{if } s < 1/3 \\ \frac{1}{2}\left[\sin\left[3\pi\left(s - \frac{1}{3}\right)\frac{\pi}{2}\right] + 1\right] & \text{if } 1/3 < s < 2/3 \\ 0.0 & \text{otherwise} \end{cases} \quad (5)$$

In contrast to the uniform depth distribution $\Phi_H(s)$ of the main fibers 31, the number of cross-linked fibers 32 continuously decreases with the depth s in the cornea 34. A person skilled in the art will understand that a different depth distribution function $\Phi_C(s)$ which decreases with depth s can also be used for the cross-linked fibers 32 on account of different anatomical circumstances.

Since parts of the transition 36 from the cornea to the sclera 35 are corneal tissue, the fiber distribution and the consideration of the depth inhomogeneity is also applied in the transition 36. In the transition 36 from the patient-specific cornea 34 to the population-based sclera 35, the cross-linked fibers 32 are also distributed in the same manner as in the cornea 34. Within the layers extending parallel to the front/outer surface of the transition 36 defined by the function $M_A(R,\varphi)$, the cross-linked fibers 32 are distributed (in plane) by means of the two-dimensional distribution function $\Phi_{2D}$, described above, in accordance with equations (1) to (3). The inhomogeneous depth distribution is derived from the depth distribution in accordance with equation (5). Here, $t(R,\varphi) = M_A(R,\varphi) - M_F(R,\varphi)$ and hence $$\Phi_C(t) = \begin{cases} 0.0 & \text{if } t < 1/3 \\ \frac{1}{2}\left[\sin\left[3\pi\left(t - \frac{1}{3}\right)\frac{\pi}{2}\right] + 1\right] & \text{if } 1/3 < t < 2/3 \\ 1.0 & \text{otherwise} \end{cases} \quad (6)$$

applies. The inhomogeneous depth distribution of the cross-linked fibers 32 is depicted schematically in FIGS. 6 and 7 in such a way that the cross-linked fibers 32 are depicted as inclined arrows, the length of which symbolizes the weighting (number, frequency) thereof.

Refractive surgical treatments, such as e.g. phototherapeutic keratectomy (PTK) and laser-assisted in situ keratomileusis (LASIK), are known to lead to peripheral corneal thickening. It is assumed that the incisions of the treatment lead to relaxation in the tissue. This relaxation in turn leads to changes in the physiological imbibition pressure of the cornea, leading to liquid displacements and the swelling of the tissue. Liquid displacements through the tissue structure of the cornea can be formulated as a poroelastic problem and it can be modeled by means of two-phase finite elements. Here, it is possible to image both the linear and the nonlinear case (in the latter case, the material permeability—i.e. the permeability of the material to liquids—depends on the deformation).

In step S24, the processor introduces permeability values into the finite element model of the cornea 34 and optionally of the transition to the sclera 35. The permeability values P(s) characterize the liquid exchange in the corneal tissue and are set dependent on the depth s of the cornea 34. The permeability values P(s) specify the permeability of the corneal tissue to liquids, dependent on the depth s of the cornea 34. Since the depth distribution function for inclined fibers is related directly to the degree of adhesion of the collagen fibers and hence to the impermeability of the tissue, the change in the permeability P(s) dependent on the depth s can be modeled in accordance with the following equation (7) as a function of the depth distribution function $\Phi_C(s)$ of the cross-linked fibers 32:

$$P(s) = 1 - \Phi_C(s). \quad (7)$$

Hence, the change in the permeability in the two-phase finite elements with the depth s in the cornea, and hence the depth-dependent swelling of the cornea, can be modeled.

The individual elements of the finite element model produced in step S2, with the initial geometry of the cornea 34 and the transition 36 to the sclera 35, each comprise a plurality of integration points with element values such as stress, strain, deformation, reaction force, plastic deformation, strain energy, etc. Here, these element values are directionally dependent values, which are calculated at the integration points from the parts contributed by the fibers. In one embodiment variant, different material properties are provided and stored in the elements for the main fibers 31 and the cross-linked fibers 32.

In step S3, the processor 10 calculates a solution to the finite element model. Here, the finite element model, produced in step S2, of the initial geometry of the cornea 34 and of the transition 36 to the sclera 35 is exposed (computationally) to the intraocular pressure (which is e.g. measured in a patient-specific manner). This leads to a (calculated) mechanical imbalance in the finite element model. As a consequence, the cornea as represented by the finite element model is deformed (inflated) and the individual elements in the model are deformed. Thus, a (calculated) strain in the elements of the model is created. The strain is connected with a defined material function which determines how much stress is created due to a calculated strain. In fact, the fibers and distribution functions are included in this material function, which is calculated at each integration point. The material function relates strain and energy (stress). The material function is defined by $$\Psi = U + \Psi_m[C_{10}] + \frac{1}{\pi}\int \Phi(\Psi_{f1}[\gamma_m, \mu_m] + \Psi_{f2}[\gamma_k, \mu_k])d\theta \quad (8)$$

where $\Psi$ is the energy, $\Psi_{f1}$ are the main fibers 31, $\Psi_{f2}$ are the cross-linked fibers 32 and $\Phi$ are the distribution functions. $\Psi_m$ is a tissue part which does not consist of fibers and U is a penalty function for changes in volume (this leads to an incompressibility of the tissue). The calculated stress is then in turn stored in the element. This sequence deformation→strain→stress is repeated iteratively in step S3 until the strain configuration at which the applied intraocular pressure is compensated for by the calculated stresses is reached. When the deformation state or the strain configuration for compensating the intraocular pressure is found for each element, there is a calculated equilibrium between stresses in the elements, which emerge from the deformation and the strain, and the intraocular pressure, i.e. a solution of the finite element model is present.

In step S4, the processor 10 graphically displays on the display 12 a three-dimensional model of the cornea 34 on the basis of the generated finite element model which is in equilibrium with the intraocular pressure. The graphical display of the corneal model can be modified by a user of the device 1, preferably by entering user commands (e.g. via mouse, keyboard and/or touchscreen), for example in respect of the orientation by means of a free rotation in space and/or in respect of the size or resolution by means of a zoom function, like in a CAD system.

In step S5, the processor 10 receives cut data, for example from a user of the device 1 in accordance with user commands and/or from a selected file with stored cut data. The user commands for defining cuts or corresponding cut data can be introduced into the displayed model by the user, for example by means of a computer mouse, a keyboard and/or by way of a touchscreen. The cut data define the three-dimensional geometry, the dimensions and the position of one or more cuts into the cornea 34 and/or in the region of the sclera 35 adjoining the cornea 34 by way of the transition 36. Here, the cuts can also be positioned in the interior of the eye tissue, with or without severing of the front/outer surface 30 of the cornea 35 or the transition surface $M_A(R,\varphi)$ of the transition 36 and the front/outer surface 350 of the sclera 35.

In step S6, the cut data are applied to the finite element model of the cornea 34 and of the transition 36 by the processor 10. That is to say, the processor 10 determines the elements in the model affected by the cut data, which elements are separated from one another by a cut carried out in accordance with the cut data.

In step S3, the processor 10 again calculates the solution to the finite element model, as described above, for the finite element model modified by the cut data. On the basis of the modified finite element model, which again is in equilibrium with the intraocular pressure, the processor 10 generates a graphical display of the corneal model modified by the cut on the display 12 in step S4.

The finite element model therefore enables the modeling of the cornea 34 and the simulation of tissue cuts in the cornea 35. Here, the degree of iteration of steps S3→S4→S5→S6→S3, or the length of cuts per iteration step, can be set e.g. by the user.

Finally, it should be noted that although the description depicts steps as being carried out in a specific sequence, a person skilled in the art will understand that the sequence of at least some steps can be modified, without in the process departing from the subject matter for which protection is sought.

The invention claimed is:

1. A computerized device for modeling a cornea for simulating tissue cuts in the cornea, comprising a processor programmed to load patient-specific corneal data, generate a patient-specific finite element model of the cornea and determine elements in the finite element model which are separated from one another by the tissue cuts on the basis of cut data defining the tissue cuts, wherein the processor is moreover programmed to distribute a first group of tissue fibers, with main fibers that extend parallel to the outer surface of the cornea, in the finite element model in accordance with a first distribution function and to distribute a second group of tissue fibers, with inclined cross-linked fibers that do not extend parallel to the outer surface of the cornea, in the finite element model in accordance with a second distribution function, wherein the second distribution function distributes the cross-linked fibers with a non-uniform, decreasing depth distribution function ($\Phi_C(s)$) over the depth (s) of the cornea, from the outer surface of the cornea to the inner surface of the cornea; and wherein said computerized device further comprises a display for graphically displaying a three-dimensional model of the cornea on the basis of the generated finite element model which is in equilibrium with the intraocular pressure.

2. The device as claimed in claim 1, wherein the processor is programmed to distribute the cross-linked fibers over the depth (s) of the cornea with a depth distribution function ($\Phi_C(s)$) having a sinusoidal profile.

3. The device as claimed in claim 2, wherein the processor is programmed to introduce permeability values for liquid exchange in the corneal tissue into the finite element model, which permeability values are dependent on the depth distribution function ($\Phi_C(s)$), by means of which the cross-linked fibers are distributed over the depth (s) of the cornea.

4. The device as claimed in claim 1, wherein the processor is programmed to introduce permeability values for liquid exchange in the corneal tissue into the finite element model, which permeability values are dependent on the depth (s) of the cornea.

5. The device as claimed in claim 1, wherein the processor is programmed to generate a transition from the patient-specific finite element model of the cornea to a population-based sclera model and to distribute the cross-linked fibers in the transition with a decreasing depth distribution function ($\Phi_C(t)$) over the depth (t) of the transition, from an outer transition surface (MA(R,φ)), which extends from the outer surface of the cornea to the outer surface of the sclera, to an inner transition surface (MP(R,φ)), which extends from the inner surface of the cornea to the inner surface of the sclera.

6. The device as claimed in claim 1, wherein the processor is programmed to distribute the cross-linked fibers on a number of layers that extend parallel to the outer surface of the cornea in the finite element model and to distribute the cross-linked fibers in the layers, respectively with a two-dimensional distribution function ($\Phi 2D$).

7. The device as claimed in claim 1, wherein the processor is programmed to store different material properties for the first group of tissue fibers and the second group of tissue fibers in the finite element model.

8. The device as claimed in claim 1, wherein the processor is programmed, in the finite element model, to distribute the main fibers uniformly on a plurality of areas that extend parallel to the outer surface of the cornea and to distribute said main fibers on the areas with in each case a two-dimensional distribution function ($\Phi 2D$).

9. A computer-implemented method for modeling a cornea for simulating tissue cuts in the cornea, which method comprises an execution of the following steps by a processor:

loading patient-specific corneal data, generating a patient-specific finite element model of the cornea, distributing a first group of tissue fibers, with main fibers that extend parallel to the outer surface of the cornea, in the finite element model in accordance with a first distribution function and distributing a second group of tissue fibers, with inclined cross-linked fibers that do not extend parallel to the outer surface of the cornea, in the finite element model in accordance with a second distribution function, wherein the second distribution function distributes the cross-linked fibers with a non-uniform, decreasing depth distribution function ($\Phi_C(s)$) over the depth (s) of the cornea, from the outer surface of the cornea to the inner surface of the cornea, and determining elements in the finite element model which are separated from one another by the tissue cuts on the basis of cut data defining the tissue cuts.

10. The method as claimed in claim 9, characterized by distributing the cross-linked fibers with a depth distribution function $\Phi_C(s)$ having a sinusoidal profile over the depth (s) of the cornea by way of the processor.

11. The method as claimed in claim 10, wherein by introducing permeability values for liquid exchange in the corneal tissue, which permeability values are dependent on the depth distribution function $\Phi_C(s)$, with which the cross-linked fibers are distributed over the depth (s) of the cornea, into the finite element model by way of the processor.

12. The method as claimed in claim 9, wherein by introducing permeability values for liquid exchange in the corneal tissue, which permeability values are dependent on the depth (s) of the cornea, into the finite element model by way of the processor.

13. The method as claimed in claim 9, wherein by generating a transition from the patient-specific finite element model of the cornea to a population-based sclera model by means of the processor and distributing the cross-linked fibers in the transition with a decreasing depth distribution function $\Phi_C(t)$ over the depth (t) of the transition, from an outer transition surface (MA(R,φ)), which extends from the outer surface of the cornea to the outer surface of the sclera, to an inner transition surface (MP(R,φ)), which inner transition surface extends from the inner surface of the cornea to the inner surface of the sclera, by way of the processor.

14. The method as claimed in claim 9, wherein by distributing the cross-linked fibers over a plurality of layers that extend parallel to the outer surface of the cornea in the finite element model by way of the processor and by distributing the cross-linked fibers in the layers, respectively with a two-dimensional distribution function, by way of the processor.

* * * * *